United States Patent
Kondo et al.

(10) Patent No.: US 8,563,774 B2
(45) Date of Patent: Oct. 22, 2013

(54) METHOD FOR PRODUCING CATALYST

(71) Applicant: Mitsubishi Rayon Co., LTD., Chiyoda-ku (JP)

(72) Inventors: Masahide Kondo, Hiroshima (JP); Masanori Nitta, Hiroshima (JP); Hiroyuki Naitou, Hiroshima (JP); Toru Kuroda, Hiroshima (JP); Seiichi Kawato, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 13/837,839

(22) Filed: Mar. 15, 2013

(65) Prior Publication Data

US 2013/0204030 A1    Aug. 8, 2013

Related U.S. Application Data

(62) Division of application No. 11/994,654, filed as application No. PCT/JP2006/313367 on Jul. 5, 2006, now Pat. No. 8,470,730.

(30) Foreign Application Priority Data

Jul. 5, 2005  (JP) .................. 2005-196582

(51) Int. Cl.
  *C07C 51/16*     (2006.01)
  *C07C 51/235*    (2006.01)
  *C07C 51/00*     (2006.01)
  *C07C 253/00*    (2006.01)
  *B01J 23/00*     (2006.01)
  *B01J 23/74*     (2006.01)

(52) U.S. Cl.
  USPC ........... 562/532; 562/534; 562/535; 562/537; 562/538; 562/542; 562/546; 562/547; 558/319; 502/321; 502/338; 502/353

(58) Field of Classification Search
  USPC ......... 562/532, 534, 535, 537, 538, 542, 546, 562/547; 558/319; 502/321, 338, 353; 134/2–3, 21, 22.1–22.19, 26–30, 36, 134/41–42
  See application file for complete search history.

(56) References Cited

U.S. PATENT DOCUMENTS

| | | | |
|---|---|---|---|
| 2,619,434 A | 11/1952 | Kraus et al. | |
| 3,457,108 A | 7/1969 | Hittel | |
| 3,485,670 A | 12/1969 | Fisher | |
| 3,522,093 A | 7/1970 | Woolman | |
| 3,679,477 A | 7/1972 | Zimmer | |
| 3,741,808 A | 6/1973 | Stalker et al. | |
| 4,713,119 A | 12/1987 | Earhart et al. | |
| 5,362,328 A | 11/1994 | Gardiner et al. | |
| 6,722,377 B1 | 4/2004 | Bruce et al. | |
| 6,770,150 B1 | 8/2004 | Duckett et al. | |
| 8,178,720 B2 | 5/2012 | Kondo et al. | |
| 8,329,942 B2 | 12/2012 | Kondo et al. | |
| 2004/0267048 A1 | 12/2004 | Kondo et al. | |
| 2005/0159619 A1 | 7/2005 | Kondo et al. | |
| 2005/0274396 A1 | 12/2005 | Shih et al. | |
| 2007/0149809 A1 | 6/2007 | Kondo et al. | |

FOREIGN PATENT DOCUMENTS

| | | |
|---|---|---|
| JP | 59-147640 | 8/1984 |
| JP | 8-309131 | 11/1996 |
| JP | 8-309192 | 11/1996 |
| JP | 2004-174487 | 6/2004 |

OTHER PUBLICATIONS

Perka, et al., "Waste Minimization in Batch Vessel Cleaning", Chem. Eng. Comm., vol. 119, pp. 167-177 (1993).

*Primary Examiner* — Anthony J Zimmer
(74) *Attorney, Agent, or Firm* — Oblon, Spivak, McClelland, Maier & Neustadt, L.L.P.

(57) ABSTRACT

Disclosed is a method for producing a catalyst, in which physical properties of a dried material or a calcined material in a production process of the catalyst are stable and a change in at least one of a catalyst activity and a selectivity to a target product is small and hence reproducibility of the catalyst is excellent. The present invention is a method for producing a catalyst containing molybdenum, bismuth, and iron, which contains the steps of washing a surface of at least one device equipped in an apparatus for the production of catalyst, to which a solid matter adheres, with a basic solution, and producing the catalyst with the apparatus for the production of catalyst thus washed.

17 Claims, No Drawings

METHOD FOR PRODUCING CATALYST

This is a divisional application of U.S. application Ser. No. 11/994,654, filed Jan. 4, 2008, which is a 371 of PCT/JP2006/313367 filed on Jul. 5, 2006.

TECHNICAL FIELD

The present invention relates to a method for producing a catalyst containing molybdenum, bismuth, and iron.

BACKGROUND ART

The catalyst containing molybdenum, bismuth, and iron is known as an oxidation catalyst which is used for producing an unsaturated aldehyde and an unsaturated carboxylic acid through gas-phase catalytic oxidation of propylene, isobutylene, tertiary butyl alcohol (hereinafter, sometimes expressed as "TBA"), or methyl tertiary butyl ether (hereinafter, sometimes expressed as "MTBE").

For example, in Patent Documents 1 and 2, a method for producing a catalyst is individually disclosed, in which a mixed liquid containing a compound which becomes a raw material of the catalyst is prepared and the resultant mixed liquid is dried and then calcined.

Patent Document 1: Japanese Patent Application Laid-Open No. Hei 8-309,191
Patent Document 2: Japanese Patent Application Laid-Open No. Hei 8-309,192

DISCLOSURE OF INVENTION

Problem to be Solved by the Invention

In a conventional method, when a catalyst is produced repeatedly, it was necessary to adjust conditions at the time of molding a dried material or a calcined material at each production batch because physical properties, such as bulk density, of a dried material of a mixed liquid or a calcined material obtained by calcining the dried material changed. Further, there was a case that at least one of a catalyst activity and a selectivity to a target product was deteriorated when the catalyst production was repeated.

Conventionally, there has been a case that a solid matter containing molybdenum, bismuth, and iron adheres to a surface of a device equipped in an apparatus for the production of catalyst when the catalyst is produced, however, such an adherence of the solid matter has not particularly been recognized as a problem. However, the present inventors have found that the solid matter is a cause of the change of the physical properties of the aforementioned bulk density or the deterioration of at least one of the catalyst activity and the selectivity to the target product, and thus they have completed the present invention.

It is an object of the present invention to provide a method for producing a catalyst, in which physical properties of a dried material or a calcined material in a production process of the catalyst are stable and a change in at least one of a catalyst activity and a selectivity to a target product is small and hence reproducibility of the catalyst is excellent.

Means for Solving the Problem

The present invention is a method for producing a catalyst comprising molybdenum, bismuth, and iron, comprising the steps of:

washing a surface of at least one device equipped in an apparatus for the production of catalyst, to which a solid matter adheres, with a basic solution; and
producing the catalyst with the apparatus for the production of catalyst thus washed.

Effect of the Invention

According to the present invention, a method for producing a catalyst, in which physical properties of a dried material or a calcined material in a production process of the catalyst are stable and a change in at least one of a catalyst activity and a selectivity to a target product is small and hence reproducibility of the catalyst is excellent, can be provided. Further, according to the present invention, the catalyst can be produced efficiently because a residual material can be reduced by saving the time of overhaul in the case that an apparatus for the production of catalyst is complicatedly assembled.

BEST MODE FOR CARRYING OUT THE INVENTION

As the catalyst containing molybdenum, bismuth, and iron to be produced in the present invention, for example, one to be used for producing an unsaturated aldehyde and an unsaturated carboxylic acid through gas-phase catalytic oxidation of propylene, isobutylene, TBA, or MTBE with molecular oxygen, or one to be used for producing acrylonitrile through gas-phase catalytic ammoxidation of propylene can be listed.

Hereinafter, the method for producing the catalyst of the present invention will be explained with reference to the method for producing the catalyst for producing an unsaturated aldehyde and an unsaturated carboxylic acid, which is one embodiment of the present invention.

The catalyst to be produced is not particularly limited as long as it contains molybdenum, bismuth, and iron, however, it is preferably the one represented by the following formula (1).

$$Mo_aBi_bFe_cM_dX_eY_fZ_gSi_hO_i \qquad (1)$$

In the formula (1), Mo, Bi, Fe, Si, and O represent molybdenum, bismuth, iron, silicone, and oxygen, respectively. M represents at least one element selected from the group consisting of cobalt and nickel. X represents at least one element selected from the group consisting of chromium, lead, manganese, calcium, magnesium, niobium, silver, barium, tin, tantalum and zinc. Y represents at least one element selected from the group consisting of phosphorus, boron, sulfur, selenium, tellurium, cerium, tungsten, antimony, and titanium. Z represents at least one element selected from the group consisting of lithium, sodium, potassium, rubidium, cesium, and thallium. a, b, c, d, e, f, g, h, and i represent an atomic ratio of each element, respectively, and when a is 12, b is from 0.01 to 3, c is from 0.01 to 5, d is from 1 to 12, e is from 0 to 8, f is from 0 to 5, g is from 0.001 to 2, h is from 0 to 20, and i is the atomic ratio of oxygen that fulfills the requirement of the valence of each element mentioned above.

In the present invention, a raw material of an element that composes the catalyst (hereinafter, expressed as a "catalyst raw material") is not particularly limited, however, usually, an oxide of the element that composes the catalyst, a chloride, a hydroxide, a sulfate, a nitrate, a carbonate, or an ammonium salt that can become the oxide of the element that composes the catalyst by ignition, or a mixture of these compounds can be used.

The production of the catalyst can be carried out, for example, by properly combining the following steps.

Blending step: A step in which a solution or a fluid dispersion containing at least one kind of the element that composes the catalyst (hereinafter, expressed as a "blended liquid") is prepared by blending at least one kind of the catalyst raw material and a liquid in a blending tank.

Mixing step: A step in which a solution or a fluid dispersion containing all the elements that compose the catalyst (hereinafter, expressed as a "raw material liquid") is prepared by mixing two or more kinds of the blended liquids or by mixing the blended liquid and another catalyst raw material in a mixing tank.

Aging step: A step in which the raw material liquid is aged while heated in an aging tank.

Concentrating step: A step in which the raw material liquid is concentrated in a concentrating tank.

Atomizing step: A step in which a solid matter contained in the raw material liquid is atomized in an atomizing tank.

There is a case that a tank equipped with a jacket with which contents of the tank can be heated or cooled is used as a device such as the blending tank, the mixing tank, the aging tank, the concentrating tank, or the atomizing tank in order to adjust the temperature of the solution or the fluid dispersion in these steps. In this case, the temperature of the contents of the tank is adjusted by causing a heating medium such as water vapor to exist or flow inside the jacket. Further, a device equipped with a heating part such as a heater or a cooling part inside can be used for the adjustment of the temperature. In the apparatus for the production of catalyst to be used in the present invention, the blending tank, the mixing tank, the aging tank, the concentrating tank, and the atomizing tank mentioned above are included, however, not only these devices but also, for example, a piping, a pump, a strainer, a stirring blade, a heater, and the like are included.

In the next place, each production step of the catalyst will be explained in detail.

(Blending Step)

In the blending step, the blended liquid is prepared by blending at least one kind of the catalyst raw material and a liquid in a blending tank. It is preferable to separate the catalyst raw material into two or more kinds and to prepare two or more kinds of the blended liquids. The method for separating the catalyst raw material into two or more kinds is not particularly limited, however, it is preferable to select a combination of the catalyst raw material and the liquid, which does not cause precipitation or gelation of the resulting blended liquid, and it is more preferable to make a blended liquid of a raw material of molybdenum and a blended liquid of a raw material of iron separately.

As the blended liquid containing molybdenum, for example, an aqueous solution obtained by dissolving ammonium molybdate in water can be listed. Further, as the blended liquid containing iron, for example, an aqueous solution obtained by dissolving respective nitrates of iron, bismuth, cobalt, and cesium in dilute nitric acid can be listed.

(Mixing Step)

In the mixing step, the raw material liquid is prepared by mixing two or more kinds of the blended liquids or by mixing the blended liquid and another catalyst raw material in a mixing tank. The other catalyst raw material means the catalyst raw material that has not been blended in the blending step, and it may be a solid such as an oxide or a salt of an element that composes the catalyst, which is the same as mentioned above. The combination of the blended liquid and the other catalyst raw material to be mixed in the mixing step is not particularly limited, however, the combination of two or more kinds of the blended liquids is preferable, the combination of two or more kinds of the blended liquids which is not causing precipitation or gelation is more preferable, and above all, the combination of the blended liquid containing molybdenum and the blended liquid containing iron is particularly preferable. As the method for mixing, for example, a method of stirring mixing or a method of ultrasonic mixing can be listed.

For example, when the blended liquid containing molybdenum and the blended liquid containing iron are mixed, there are many cases that precipitation is formed to cause gelation. In this case, precipitated particles with the same fine structure such as particle diameter can be obtained by adjusting the mixing time to a fixed value in each production batch. The mixing time on that occasion is preferably 60 seconds or more, and the catalyst can be produced with excellent reproducibility by such a mild mixing.

When the blended liquid containing molybdenum and the blended liquid containing iron are mixed, it is preferable to mix in such a way that the blended liquid containing iron is added to the blended liquid containing molybdenum.

(Aging Step)

In the aging step, the raw material liquid is aged while heated in an aging tank. It is preferable that the aging be carried out for 30 minutes or more while heated. In that case, the temperature of the raw material liquid is preferably 80 to 103° C. The aging step is not always necessary, however, in the case that the raw material liquid is a slurry containing precipitated particles, the precipitated particles grow and get stabilized by carrying out this step.

(Concentrating Step)

In the concentrating step, the raw material liquid is concentrated by heating it to evaporate the liquid in a concentrating tank. A target viscosity or a target solid content at the time when the concentration is finished is properly set according to a property of the raw material liquid or a drying method after the concentration. The concentrating step is not always necessary, however, physical properties of a dried powder can be adjusted by carrying out this step. Further, there is a case that a reaction performance of the catalyst is improved by carrying out the concentrating step.

(Atomizing Step)

In the atomizing step, a solid matter contained in the raw material liquid is atomized in an atomizing tank by using an atomizing measure such as homogenizer. The atomizing step is not always necessary, however, the reaction in the aging step is further advanced by carrying out this step.

(Drying, Heating, Molding, and the Like)

Further, a treatment such as drying, heating, and molding can be carried out, when it is needed.

A device to be used for drying is not particularly limited, and for example, a tray dryer, a spray dryer, a drum dryer, or a slurry dryer can be listed. Now, drying means an operation in which a substantially solid dried material is obtained by evaporating a part of or all the liquid from the raw material liquid. A drying temperature is preferably 30 to 150° C. in the case of the tray dryer, and 100 to 500° C. as an inlet temperature in the case of the spray dryer. A shape of the dried material is not particularly limited, and for example, a shape such as powder or block can be listed.

In the case that the dried material does not have catalyst activity or improvement of the catalyst activity is desired, it is possible to give the catalyst activity by heating the dried material. A method for heating is not particularly limited, however, for example, a method of preliminary calcining at the temperature range of from 200 to 400° C. for about 1 to 5 hours followed by calcining at the temperature range of from 400 to 650° C. for about 1 to 20 hours is preferable.

In the case of producing a molded catalyst, a dried material, a dried material preliminary calcined, or a calcined material may be molded at an appropriate stage. A method for molding is not particularly limited, and for example, a molding method such as a supporting molding, a pelleting molding, or an extrusion molding can be adopted.

(The Step of Washing with the Basic Solution)

In the present invention, a surface of at least one device equipped in an apparatus for the production of catalyst is washed with a basic solution.

The surface of at least one device equipped in the catalyst production apparatus means a surface to which a catalyst raw material to be introduced at the time of catalyst production, a catalyst precursor, or a catalyst contacts. For example, an inner wall of a tank such as a blending tank, a mixing tank, an aging tank, a concentrating tank, or an atomizing tank; a surface of an internal device such as a stirring device or a heater used in the tank; an inner surface of an accessory device such as a strainer or a pump attached to the tank; an inner wall of a piping connected to the tank; a surface of a dryer which contacts with a material to be dried or a dried material; or a surface of a molding machine which contacts with a material to be molded or a molded material can be listed.

A solution or a slurry containing raw materials of molybdenum, bismuth, and iron and the like adheres to or remains in the form of pool on the surface of such a device. There are many cases that such a liquid residue becomes a solid matter and adheres to the surface of the device after dried. Further, there is a case that a solid matter deposits on the surface of the device from the solution or the slurry containing the raw materials and adheres to the surface of the device during the catalyst production or after the catalyst production. Further, there is a case that an adherence to the surface of the device occurs through a contact with a solid matter already attached to the surface of the device. The solid matter usually contains molybdenum, bismuth, and iron. When the catalyst is produced again by using a device having a solution, a slurry, or a solid matter containing a catalyst raw material in various states (hereinafter, also expressed collectively as a "residual material") on the surface of the device, the catalyst raw material introduced, the solution or the slurry each of which contains the catalyst raw material, the catalyst precursor, or the catalyst contacts to the surface of the device. In the case of producing the catalyst using a device having such a residual material on the surface, the present invention is characterized by previously washing the surface of the device with a basic solution.

In the present invention, surfaces of all the devices having the residual material may be washed with the basic solution, however, for example, only specific devices such as a blending tank, a mixing tank, an aging tank, and a concentrating tank (hereinafter, expressed collectively as "tanks") may be washed. The present invention is effective when washing with the basic solution is carried out to the tanks, and particularly effective when the washing with the basic solution is carried out to any one of the mixing tank, the aging tank, and the concentrating tank. In this case, when there are internal devices (a stirring blade and the like) of the tanks to be washed, it is preferable to wash these internal devices and piping together with the tanks. Further, the present invention is effective when the residual material is existing on the surface of the device as a solid matter. As such a solid matter, for example, one in which bismuth and iron form a solid solution with molybdenum trioxide can be listed.

When the amount of the residual material existing on the surface of the device (including the surface of the internal device when there is the internal device) becomes large, there is a case that bulk density of the catalyst powder obtained by at least one of drying and calcining the raw material liquid increases and it becomes difficult to produce the catalyst powder with excellent reproducibility. Further, there is a case that the catalyst produced from such a catalyst powder has a low activity. These tendencies become more prominent when the amount of the residual material exceeds 50 g per 1 $m^3$ of the volume of the device. As this reason, it is presumed that a particle having a seed crystal of the residual material generate in the raw material liquid and this particle cause the increase in the bulk density and the lowering of the catalyst activity. Consequently, the present invention is preferable when the amount of the residual material exceeds 50 g per 1 $m^3$ of the volume of the device, and more preferable when the amount of the residual material exceeds 100 g per 1 $m^3$ of the volume of the device.

In the present invention, the surface of the device, on which the residual material is existing, is washed with a basic solution. The method of washing is not particularly limited as long as the basic solution contacts with the residual material, however, in the case of the tanks, a method of introducing the basic solution in the tanks and then leaving the solution to stand or fluidizing the solution can be listed. When there is an internal device having the residual material on the surface, it is preferable that washing be carried out in the state of producing the catalyst, namely, in the state that the internal device is equipped. As the method of fluidizing the solution, for example, a method of rotating a stirring blade or a method of circulating a liquid with a pump can be listed.

The basic solution is not particularly limited as long as it is the one obtained by dissolving a basic substance in a solvent. The basic substance contained in the basic solution may be one kind or two or more kinds. As the solvent of the basic solution, water, alcohol, or the like can be listed, and water is preferable. As the basic substance, for example, an oxide, a hydroxide, a carbonate, or a bicarbonate of an alkaline metal such as lithium, sodium, potassium, or rubidium; or an oxide or a hydroxide of an alkaline earth metal such as magnesium, calcium, strontium, or barium can be listed. As the basic substance, at least one kind selected from the group consisting of an oxide, a hydroxide, a carbonate, and a bicarbonate of an alkaline metal is preferable, and a hydroxide of an alkaline metal is particularly preferable. Further, as the alkaline metal, potassium is preferable.

The concentration of the basic substance in the basic solution is preferably 1 to 10% by mass, and more preferably 2 to 6% by mass.

The temperature of the basic solution to be used for washing can be optionally selected taking account of the extent of dissolution of the residual material and the like, however, it is preferably 40 to 80° C. in point of washing effect, and more preferably 50 to 70° C.

The washing time is not particularly limited as long as it is enough for reducing the residual material, however, it is preferable to continue the washing till the amount of the residual material existing on the surface of the device becomes 50 g or less per 1 $m^3$ of the volume of the device, more preferable to continue the washing till the amount of the residual material existing on the surface of the device becomes 30 g or less, and furthermore preferable to continue the washing till the residual material is perfectly removed or dissolved. It is preferable to continue the washing till the amount the residual material existing on the surface of the device finally falls within the above range because a postwashing carried out after the washing with the basic solution cannot substantially remove the residual material. The concrete washing time is variable depending on a kind or an amount of the residual material, or on a kind or an amount of the basic solution, and cannot be absolutely said, however, generally, it is preferably 1 to 5 hours and more preferably 2 to 4 hours.

This washing can be carried out any one of under pressure above atmospheric pressure, under atmospheric pressure, and under reduced pressure below atmospheric pressure. It is preferable to carry out under the reduced pressure from the viewpoint of absorption of vapor generated by heating, and the like. The pressure inside the device when the washing is carried out under the reduced pressure is preferably −0.05 to −0.001 MPa (gauge pressure).

Whether the residual material has been reduced by washing or not can be judged through examination such as visual inspection of the surface of the device which was washed.

The mechanism of the reduction of the residual material by washing with the basic solution is not clear, however, it is presumed that, when the residual material contain a solid matter of a nitrate, the nitrate react with a basic substance to form a neutral salt which gradually removes or dissolves from the surface of the device into the basic solution.

In the case that the basic solution, even though once used for washing, has an ability to remove or dissolve the residual material, it is preferable to reuse the basic solution in the next washing with the basic solution because it can reduce waste.

(Postwashing Step by a Solvent)

In the present invention, it is preferable that washing a surface of a device with a solvent (hereinafter, expressed as a "postwashing") be carried out after washing of the surface of the device with the basic solution be carried out. The method for the postwashing is not particularly limited as long as the solvent contacts with the surface of the device which is washed with the basic solution, however, in the case of the postwashing of the tanks, a method of introducing the solvent in the tanks and then leaving the solvent to stand or fluidizing the solvent can be listed. In the case that the device has an internal device and washing with the basic solution has been carried out in the state that the internal device is equipped, it is preferable that the postwashing be carried out in the state that the internal device is equipped. As the method for fluidizing the solvent, for example, a method of rotating a stirring blade or a method of circulating a liquid with a pump can be listed.

The solvent to be used for the postwashing is not particularly limited as long as it can remove a metal ion contained in the basic solution such as an alkaline metal or an alkaline earth metal, however, water is preferable. As the water, for example, a pure water, an ion-exchanged water, a distilled water, or a running water can be listed, however, one that contains little amount of sodium ion or calcium ion is preferable. The electric conductivity at 25° C. of the water to be used for the postwashing is more preferably not more than 10 mS/m and particularly preferably not more than 1 mS/m.

The temperature of the solvent to be used for the postwashing can be optionally selected taking account of the extent of remaining amount of the basic solution and the like, however, it is preferably within the range of from 20° C. to the boiling point of the solvent in point of washing effect, and more preferably within the range of from 50° C. to the boiling point of the solvent.

When the postwashing is carried out using water as the solvent, namely, washing with water is carried out, it is preferable to continue or repeat the washing with water till pH of the wastewater at 50° C. after the washing with water becomes 9 or less, more preferable to continue or repeat till pH at 50° C. becomes 4 to 9, and furthermore preferable to continue or repeat till pH at 50° C. becomes 6 to 8. Further, it is preferable to continue or repeat the postwashing till the sum of concentrations of an alkaline metal and an alkaline earth metal in the wastewater becomes 50 mg/liter or less, and more preferable to continue or repeat till the sum becomes 10 mg/liter or less.

The postwashing can be carried out any one of under pressure above atmospheric pressure, under atmospheric pressure, and under reduced pressure below atmospheric pressure. It is preferable to carry out under the reduced pressure from the viewpoint of absorption of vapor generated by heating, and the like. The pressure inside the device when the postwashing is carried out under the reduced pressure is preferably −0.05 to −0.001 MPa (gauge pressure).

(Prewashing Step by a Solvent)

In the present invention, it is preferable that washing a surface of a device with a solvent (hereinafter, expressed as a "prewashing") be previously carried out before washing of the surface of the device with the basic solution be carried out. The method for the prewashing is not particularly limited as long as the solvent contacts with the surface of the device having the residual material, however, in the case of the prewashing of the tanks, a method of introducing the solvent in the tanks and then leaving the solvent to stand or fluidizing the solvent can be listed. In the case that there is an internal device having the residual material on the surface, it is preferable that the prewashing be carried out in the state that the internal device is equipped. As the method for fluidizing the solvent, for example, a method of rotating a stirring blade or a method of circulating a liquid with a pump can be listed.

The solvent to be used for the prewashing is preferably one that can remove or dissolve a part of the residual material, and more preferably water. As the water, for example, a pure water, an ion-exchanged water, a distilled water, or a running water can be listed, however, one that contains little amount of sodium ion or calcium ion is preferable. The electric conductivity at 25° C. of the water to be used for the prewashing is preferably not more than 10 mS/m and particularly preferably not more than 1 mS/m. It is preferable to remove a part of the residual material by the prewashing because it can reduce the amount of the basic solution to be used.

The temperature of the solvent to be used for the prewashing can be optionally selected taking account of the extent of dissolution of the residual material and the like, however, it is preferably within the range of from 20° C. to the boiling point of the solvent in point of washing effect, more preferably within the range of from 50° C. to the boiling point of the solvent, and particularly preferably within the range of from 80° C. to the boiling point of the solvent.

The prewashing can be carried out any one of under pressure above atmospheric pressure, under atmospheric pressure, and under reduced pressure below atmospheric pressure. It is preferable to carry out under the reduced pressure from the viewpoint of absorption of vapor generated by heating, and the like. The pressure inside the device when the prewashing is carried out under the reduced pressure is preferably −0.05 to −0.001 MPa (gauge pressure).

(Method for Using the Catalyst)

In the next place, the method for using the catalyst will be explained. It is preferable that the catalyst be used in a molded form or a supported form in a fixed bed, however, the catalyst may be used in a particle form in a fluidized bed. Reaction conditions will be explained using, as an example, the cases in which, by using this catalyst, an oxidation reaction of isobutylene, TBA, or MTBE (hereinafter, also expressed collectively as "isobutylene or the like") to methacrolein and methacrylic acid (hereinafter, also expressed collectively as "methacrolein and the like") and an oxidation reaction of propylene to acrolein and acrylic acid (hereinafter, also expressed collectively as "acrolein and the like") are carried out.

When the oxidation reaction of the isobutylene or the like to the methacrolein and the like is carried out, a feed gas containing the isobutylene or the like and molecular oxygen is brought into contact with the catalyst. The concentration of the isobutylene or the like in the feed gas is preferably 1 to 20% by volume, and the molar ratio of the isobutylene or the like to oxygen is preferably 1/0.5 to 1/3. Water vapor may be added to the feed gas, and the concentration of the water vapor is preferably 1 to 45% by volume. Further, the reaction pressure is preferably 0 to 300 kPa (gauge pressure), and the reaction temperature is preferably 250 to 400° C., and the contact time is preferably 1.5 to 15 seconds.

When the oxidation reaction of propylene to acrolein and the like is carried out, a feed gas containing propylene and molecular oxygen is brought into contact with the catalyst. The concentration of propylene in the feed gas is preferably 1 to 20% by volume, and the molar ratio of propylene to oxygen is preferably 1/0.5 to 1/3. Water vapor may be added to the feed gas, and the concentration of the water vapor is preferably 1 to 45% by volume. Further, the reaction pressure is preferably 0 to 300 kPa (gauge pressure), and the reaction temperature is preferably 250 to 400° C., and the contact time is preferably 1.5 to 15 seconds.

EXAMPLES

Hereinafter, the present invention will be explained by examples and comparative examples.

Isobutylene conversion, selectivity to methacrolein, selectivity to methacrylic acid, and total yield of methacrolein and methacrylic acid (hereinafter, expressed as a "total yield") were calculated by the following formulae.

Isobutylene conversion (%)=$(A/B) \times 100$

Selectivity to methacrolein (%)=$(C/A) \times 100$

Selectivity to methacrylic acid (%)=$(D/A) \times 100$

Total yield (%)=$\{(C+D)/B\} \times 100$

In the above formulae, A represents number of moles of isobutylene reacted, B represents number of moles of isobutylene supplied, C represents number of moles of methacrolein produced, and D represents number of moles of methacrylic acid produced. The analysis was carried out using gas chromatography.

Further, reaction rate (catalyst activity) per mass of catalyst is a flow rate of a raw material per mass of catalyst and time (NL/kg·h) under the conditions that reaction temperature is fixed and conversion of isobutylene which is a raw material is approximately fixed.

Reference Example 1

To blending tank 1, 1,000 parts of pure water was introduced, and 500 parts of ammonium paramolybdate, 18.5 parts of ammonium paratungstate, 24.1 parts of antimony trioxide, 14.3 parts of potassium nitrate, and 496.3 parts of 20% by mass silica sol were added, and the resultant mixture was heated while stirred to prepare liquid A which is a blended liquid.

To blending tank 2, 850 parts of pure water was introduced, and 250 parts of 60% by mass nitric acid was added and the resultant solution was made homogeneous, and 57.2 parts of bismuth nitrate was added and dissolved. To the resultant solution, 228.8 parts of ferric nitrate, 494.4 parts of cobalt nitrate, and 77.2 parts of zinc nitrate were successively added and dissolved to prepare liquid B which is a blended liquid.

Using the blending tank 1 as a mixing tank, the liquid B was added while the liquid A was stirred to obtain a raw material liquid in a state of slurry. The raw material liquid was transferred to a aging tank, heated to 95° C., and aging of the raw material liquid was carried out for 90 minutes. Subsequently, using the aging tank as a concentrating tank, concentration of the raw material liquid which had been aged was carried out at 103° C.

Subsequently, the concentrated raw material liquid was drawn out from the concentrating tank, and made into dried spherical particles using a spray dryer. The spherical particles were preliminarily calcined at 300° C. for 1 hour, and further calcined at 500° C. for 3 hours to obtain a calcined catalyst (catalyst powder). The average particle diameter of the calcined catalyst was 54 μm, and the bulk density of the calcined catalyst was 1.00 g/ml. The average particle diameter was measured by laser diffraction type and on the basis of volume, and the bulk density was measured according to the method described in JIS K6721.

To 500 parts of the calcined catalyst, 15 parts of methyl cellulose was added and dryblended. To the resultant mixture, 180 parts of pure water was added and mixed (kneaded) with a kneader, and then extrusion molded with a piston type extrusion molder to obtain ring shaped molded articles of external diameter of 5 mm, internal diameter of 2 mm, and length of 5 mm.

The resultant molded articles were dried at 110° C. with a circulating hot air dryer, and calcined again at 400° C. for 3 hours to obtain a catalyst. The composition of elements excluding oxygen of the catalyst thus obtained was $Mo_{12}Bi_{0.5}Fe_{2.4}Co_{7.2}Zn_{1.1}Sb_{0.7}Si_7W_{0.3}K_{0.5}$.

The catalyst was packed in a stainless steel reaction tube and reaction was carried out using a feed gas containing 5% of isobutylene, 12% of oxygen, 10% of water vapor, and 73% of nitrogen (volume %), under the conditions of under atmospheric pressure, contact time of 3.6 seconds, and reaction temperature of 340° C., until isobutylene conversion became 95%. As a result, the selectivity to methacrolein was 88.8%, the selectivity to methacrylic acid was 4.0%, the total yield of methacrolein and methacrylic acid was 88.2%, and the catalyst activity was 2,300 NL/kg·h.

Example 1

On the surfaces of the blending tank 1 and the aging tank used for the catalyst production in Reference Example 1 (including the surface of a stirring device equipped inside), 120 g of the residual material containing molybdenum, bismuth, and iron per 1 $m^3$ of each volume of the blending tank 1 and the aging tank existed, respectively. The fact that molybdenum, bismuth, and iron were contained in the residual material was confirmed with ICP spectrometry. Further, the amount of the residual material was quantitatively determined in such a way that the catalyst was previously produced by separately carrying out the same operation, and the residual material was carefully scraped up from the surfaces of the blending tank 1 and the aging tank.

To the blending tank 1, on the surface of which there exists the residual material, 0.98 time as much as the volume of the blending tank 1 of pure water at 60° C. (electric conductivity at 25° C. being 4 mS/m) was introduced, and a prewashing was carried out once for 60 minutes under stirring. The prewashing was carried out once adjusting the pressure inside the blending tank 1 to −0.01 MPa (gauge pressure).

Subsequently, after all the pure water used for the prewashing in the blending tank 1 was discharged, 0.98 time as much as the volume of the blending tank 1 of 4% by mass potassium hydroxide aqueous solution at 60° C. was introduced to the blending tank 1, and the blending tank 1 was washed for 1 hour while stirred with a stirrer. The washing with a basic solution was carried out adjusting the pressure inside the blending tank 1 to −0.01 MPa (gauge pressure).

Subsequently, after all the potassium hydroxide aqueous solution used for washing in the blending tank 1 was discharged, 0.98 time as much as the volume of the blending tank 1 of pure water at 100° C. (electric conductivity at 25° C. being 4 mS/m) was introduced to the blending tank 1, and a postwashing was carried out once for 60 minutes under stirring. The postwashing was carried out adjusting the pressure inside the blending tank 1 to −0.01 MPa (gauge pressure).

The pH of the wastewater at 50° C. after the postwashing was 6.2, and the total concentration of an alkaline metal and an alkaline earth metal in the wastewater was 22 mg/liter. Further, the amount of the residual material, containing molybdenum, bismuth, and iron, existing on the surface of the inner wall of the blending tank 1 after the postwashing was 36 g per 1 m$^3$ of the volume of the blending tank 1.

Further, washing of the aging tank was carried out using the same procedure as in washing of the blending tank 1. As a result, the pH of the wastewater at 50° C. after the postwashing was 6.5, and the total concentration of an alkaline metal and an alkaline earth metal in the wastewater was 25 mg/liter. Further, the amount of the residual material, containing molybdenum, bismuth, and iron, existing on the surface of the inner wall of the aging tank after the postwashing was 40 g per 1 m$^3$ of the volume of the aging tank.

Using the blending tank 1 and the aging tank washed as mentioned above, the catalyst was produced in the same manner as in Reference Example 1, and the reaction producing methacrolein and methacrylic acid from isobutylene was carried out.

Example 2

The blending tank 1 and the aging tank which were used for producing the catalyst in Example 1 were washed in the same manner as in Example 1. The states of the wastewater after washing, the blending tank 1, and the aging tank were about the same as those in the case of Example 1. The same procedure as in Reference Example 1 was carried out except that the blending tank 1 and the aging tank thus washed were used, and the catalyst of the second batch was produced, and the reaction producing methacrolein and methacrylic acid from isobutylene was carried out.

Example 3

The blending tank 1 and the aging tank which were used for producing the catalyst in Example 2 were washed in the same manner as in Example 1. The states of the wastewater after washing, the blending tank 1, and the aging tank were about the same as those in the case of Example 1. The same procedure as in Reference Example 1 was carried out except that the blending tank 1 and the aging tank thus washed were used, and the catalyst of the third batch was produced, and the reaction producing methacrolein and methacrylic acid from isobutylene was carried out.

Example 4

The blending tank 1 and the aging tank which were used for producing the catalyst in Example 3 were washed in the same manner as in Example 1. The states of the wastewater after washing, the blending tank 1, and the aging tank were about the same as those in the case of Example 1. The same procedure as in Reference Example 1 was carried out except that the blending tank 1 and the aging tank thus washed were used, and the catalyst of the fourth batch was produced, and the reaction producing methacrolein and methacrylic acid from isobutylene was carried out.

Reference Example 2

The catalyst was produced in totally the same manner as in Reference Example 1, and the reaction producing methacrolein and methacrylic acid from isobutylene was carried out.

Comparative Examples 1 to 4

Washing was carried out in the same manner as in Example 1 except that the blending tank 1 and the aging tank which were used for producing the catalyst in Reference Example 2 were washed with pure water (electric conductivity at 25° C. being 4 mS/m) instead of 4% by mass potassium hydroxide aqueous solution. The same procedure as in Reference Example 1 was carried out except that the blending tank 1 and the aging tank thus washed were used, and the catalyst was produced, and the reaction producing methacrolein and methacrylic acid from isobutylene was carried out (Comparative Example 1). Further, the same procedures were repeatedly carried out in washing of the blending tank 1 and the aging tank, production of the catalyst, and the reaction producing methacrolein and methacrylic acid from isobutylene as in Examples 2 to 4, except that pure water was used instead of 4% by mass potassium hydroxide aqueous solution (Comparative Examples 2 to 4). The amount of a material adhered to the blending tank 1 and the aging tank increased as the number of times of the batch.

The results of the examples and the comparative examples mentioned above are collectively shown in Table 1.

TABLE 1

| | Catalyst activity (NL/kg · h) | Selectivity to methacrolein (%) | Selectivity to methacrylic acid (%) | Total yield (%) | Bulk density of catalyst powder (g/ml) |
|---|---|---|---|---|---|
| Reference Ex. 1 | 2,300 | 88.8 | 4.0 | 88.2 | 1.00 |
| Example 1 | 2,250 | 88.7 | 4.0 | 88.1 | 0.99 |
| Example 2 | 2,310 | 88.7 | 4.1 | 88.2 | 0.99 |
| Example 3 | 2,330 | 88.7 | 4.1 | 88.2 | 1.00 |
| Example 4 | 2,290 | 88.8 | 3.9 | 88.1 | 0.98 |
| Reference Ex. 2 | 2,300 | 88.8 | 4.0 | 88.2 | 1.00 |
| Comparative Ex. 1 | 1,396 | 88.6 | 4.0 | 88.0 | 1.10 |
| Comparative Ex. 2 | 1,793 | 88.5 | 3.9 | 87.8 | 1.13 |
| Comparative Ex. 3 | 2,100 | 88.5 | 3.8 | 87.7 | 1.15 |
| Comparative Ex. 4 | 1,150 | 88.4 | 3.8 | 87.6 | 1.19 |

In the examples, the catalyst activity, the selectivity to methacrolein, and the selectivity to methacrylic acid were obtained with excellent reproducibility. Further, the bulk density of the catalyst powder was stable. On the other hand, in the comparative examples, the catalyst activity, the selectivity to methacrolein, and the selectivity to methacrylic acid were bad in reproducibility, and the bulk density of the catalyst powder became larger as the number of times of the batch.

What is claimed is:

1. A method for producing an unsaturated aldehyde and an unsaturated carboxylic acid through gas-phase catalytic oxidation of propylene, isobutylene, tertiary butyl alcohol, or methyl tertiary butyl ether with molecular oxygen in the presence of a catalyst comprising molybdenum, bismuth, and iron; which method comprises:
   (1) a washing step consisting of the following (a) and (b):
   (a) washing a surface of at least one device equipped in an apparatus for the production of the catalyst, to which a solid matter including molybdenum, bismuth and iron adheres, with a basic solution having a basic substance concentration of 1 to 6% by mass;
   (b) sequentially washing the surface of the device, which was washed with the basic solution, only with water to remove the basic solution; and
   (2) a step of producing the catalyst with the apparatus for the production of catalyst thus washed; and
   (3) conducting said gas-phase catalytic oxidation in the presence of the catalyst from step (2).

2. A method for producing an unsaturated nitrile through gas-phase catalytic ammoxidation of propylene, isobutylene, or tertiary butyl alcohol with molecular oxygen and ammonia in the presence of a catalyst comprising molybdenum, bismuth, and iron;
   which method comprises:
   (1) a washing step consisting of the following (a) and (b):
   (a) washing a surface of at least one device equipped in an apparatus for the production of the catalyst, to which a solid matter including molybdenum, bismuth and iron adheres, with a basic solution having a basic substance concentration of 1 to 6% by mass;
   (b) sequentially washing the surface of the device, which was washed with the basic solution, only with water to remove the basic solution; and
   (2) a step of producing the catalyst with the apparatus for the production of catalyst thus washed; and
   (3) conducting said gas-phase catalytic ammoxidation in the presence of the catalyst from step (2).

3. The method according to claim 1 or 2, wherein the basic solution is the one obtained by dissolving at least one selected from the group consisting of an oxide, a hydroxide, a carbonate, and bicarbonate of an alkaline metal, and an oxide and a hydroxide of an alkaline earth metal in a solvent.

4. The method according to claim 1 or 2, wherein the washing with the basic solution is carried out until the solid matter adhering to the surface of the device to be washed in the step of washing with the basic solution becomes 50 g or less per 1 $m^3$ of the volume of the device.

5. The method according to claim 1 or 2, wherein
   the device to be washed in is selected from the group consisting of a mixing tank in which a raw material liquid comprising all the elements composing the catalyst is prepared, an aging tank in which the raw material liquid is aged while heated, and a concentrating tank in which the raw material liquid is concentrated, and wherein an internal device and a piping of the device are washed together.

6. The method according to claim 1 or 2, wherein washing with the basic solution is carried out under reduced pressure.

7. The method according to claim 1 or 2, wherein the water has an electric conductivity of not more than 10 mS/m.

8. The method according to claim 1 or 2, wherein the washing with water is carried out until pH of a wastewater at 50° C. becomes 9 or less.

9. The method according to claim 1 or 2, wherein the washing with water is carried out until a total concentration of an alkaline metal and an alkaline earth metal in the wastewater becomes 50 mg/liter or less.

10. The method according to claim 1 or 2, wherein the washing with water is carried out under reduced pressure.

11. The method according to claim 1 or 2, wherein the basic solution has a basic substance concentration of 2 to 6% by mass.

12. The method according to claim 1 or 2, wherein the solid matter exceeds 50 g per 1 $m^3$ of the volume of the device.

13. The method according to claim 1 or 2, wherein the solid matter exceeds 100 g per 1 $m^3$ of the volume of the device.

14. The method according to claim 1 or 2, wherein washing with the basic solution is carried out at a basic solution temperature of from 40 to 80° C.

15. The method according to claim 1 or 2, wherein washing with the basic solution is carried out at a basic solution temperature of from 50 to 70° C.

16. The method for producing a catalyst according to claim 8, wherein the pH is 4 to 9.

17. The method for producing a catalyst according to claim 8, wherein the pH is 6 to 8.

* * * * *